United States Patent [19]
Hilton

[11] Patent Number: 6,007,001
[45] Date of Patent: Dec. 28, 1999

[54] AUTOFOG NOZZLE

[75] Inventor: Thomas J. Hilton, Kirkland, Wash.

[73] Assignee: Amhi Corporation, Kirkland, Wash.

[21] Appl. No.: 09/049,607

[22] Filed: Mar. 27, 1998

Related U.S. Application Data

[60] Provisional application No. 60/069,936, Dec. 17, 1997.

[51] Int. Cl.⁶ ....................................................... B05B 1/32

[52] U.S. Cl. ........................................... 239/452; 239/456

[58] Field of Search ................................... 239/451, 452, 239/456–460

[56] References Cited

U.S. PATENT DOCUMENTS

| | | | |
|---|---|---|---|
| 3,387,791 | 6/1968 | Allenbaugh, Jr. | 239/460 X |
| 4,653,693 | 3/1987 | Steingass | 239/460 |

Primary Examiner—Andres Kashnikow
Assistant Examiner—Sean P. O'Hanlon
Attorney, Agent, or Firm—Christensen O'Connor Johnson & Kindness PLLC

[57] ABSTRACT

A nozzle (10) for emitting water, for the purpose of extinguishing fires for example, generally includes a main housing (12) for housing a barrel (62), a deflector (64), and a carrier (60). The barrel (62) supports the deflector (64) and is disposed inside of the carrier (60). When water is supplied to the nozzle (10), a locking pin (59) engages a helical groove (80) on the carrier (60). When the locking pin (59) is engaged, rotation of a spray ring assembly (18) coaxially installed around the upstream end of the nozzle (10) causes the carrier (60) and the spray ring assembly (18) to translate forward or to retract, depending on the direction of the rotation. When the carrier (60) and the spray ring assembly (18) are translated forward to the jet position, water exits the nozzle (10) as a concentrated jet stream. When the carrier (60) and the spray ring assembly (18) are retracted to the fog position, water exits the nozzle (10) as a less concentrated water spray. If the water pressure falls below a predetermined level, the locking pin (59) disengages and a carrier spring (90) between the barrel (62) and the carrier (60) causes the carrier (60) and the spray ring assembly (18) to automatically retract to the fog position.

15 Claims, 7 Drawing Sheets

AUTOFOG NOZZLE

CROSS REFERENCE TO RELATED APPLICATION

The present application claims the benefit of U.S. Provisional Application Ser. No. 60/069,936 filed Dec. 17, 1997.

FIELD OF THE INVENTION

The present invention relates to a nozzle for emitting water, and more particularly, to a nozzle that can be manually adjusted from a focused jet position to a widely dispersed fog position, and that automatically returns to the fog position upon loss of water pressure.

BACKGROUND OF THE INVENTION

Commercial fire fighting nozzles for emitting water, such as those used on petroleum oil rigs, are typically adjustable between a jet position and a fog position. Such a nozzle may be secured to a hand-line, i.e. a hose, or to a monitor, i.e. a fixed structure. In the jet position, the nozzle emits a concentrated jet stream of water, whereas in the fog position, the nozzle emits a less concentrated, dispersed water spray. Hoses to which a nozzle is secured experience substantial backlash forces, and tend to whip violently if not restrained. The backlash is ameliorated when the nozzle is in the fog position. Upon loss of water pressure, it is desirable for the nozzle to automatically assume the fog position. Automatic return to the fog position upon loss of water pressure elminates hazardous situations that would otherwise arise if the nozzle were in the jet position when the water pressure subsequently returns.

One type of conventional nozzle has an inner tubular body that is moved longitudinally within an outer tubular body, such as the nozzle disclosed in WO 95/17926 applied for by Norfass A.S. in the name of inventor David A. Hill. This nozzle has several drawbacks. To assume the jet position, the inner body, along with a flow deflector, translates in a direction opposite of the flow of the water. Therefore, the inner body and the deflector must overcome the water pressure, making it more difficult to assume the jet position. Furthermore, this nozzle has a large number of parts, thereby adding to its complexity.

SUMMARY OF THE INVENTION

The present invention is a nozzle for emitting water. The nozzle generally includes a tubular carrier, a tubular barrel, a conical deflector, and a spray ring assembly. The spray ring assembly is attached to the carrier, preferably by screws. The barrel, which is attached to the deflector, is disposed inside the carrier. A carrier spring is disposed between the barrel and the carrier. When water is supplied to the nozzle, water pressure is also supplied to a bypass passageway leading to a locking pin. The water pressure displaces the locking pin to engage a helical groove on the carrier. Rotation of the spray ring assembly causes rotation of the carrier. When the locking pin is engaged in the helical groove of the carrier, rotation of the carrier causes the carrier, and thus also the spray ring assembly, to translate forward or to retract, depending on the direction of rotation.

When the carrier and the spray ring assembly translate forward to the jet position, the stream of water is converged by the straight interior side of the carrier and thus, exits the nozzle in a concentrated jet stream. When the carrier and the spray ring assembly retract to the fog position, the stream of water is directed to diverge outwardly by the outwardly slanting surface of the deflector and the outwardly slanting surface of the front end of the barrel and thus, exits the nozzle in a less concentrated water spray. When the water pressure falls below a predetermined level, the locking pin is disengaged and the carrier spring assembly causes the carrier to retract to the fog position. With the locking pin disengaged, rotation of the spray ring will cause rotation of the carrier, but will not cause translation of the carrier or the spray ring assembly. Therefore, the nozzle cannot be returned to the jet position until the water pressure is restored.

The present invention thus provides a nozzle that is more readily adjusted without having to overcome the force of supplied water pressure. Fewer component parts are required than for the conventional nozzles, which facilitates manufacture and maintenance.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
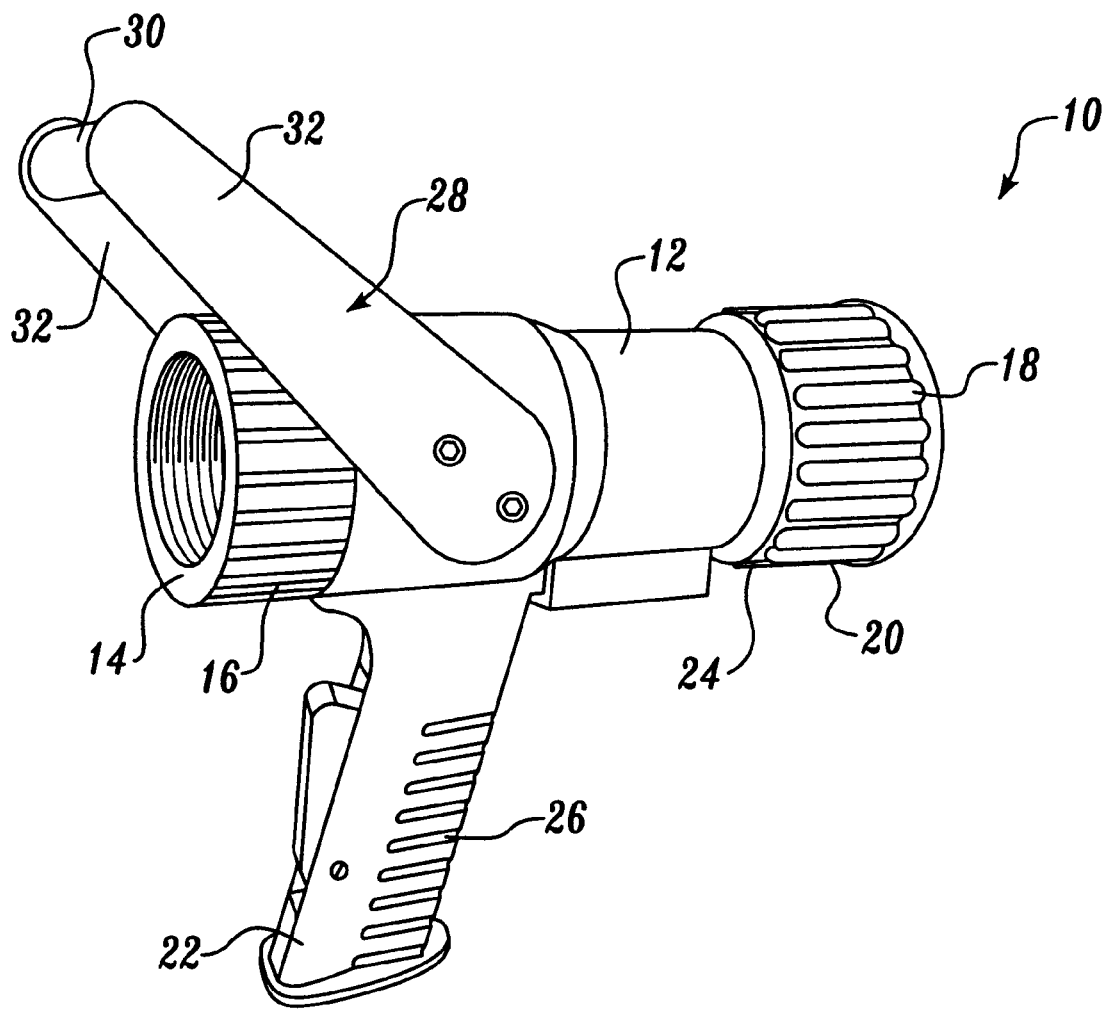
FIG. 1 is a perspective view of an autofog nozzle according to the present invention.

Referring to FIG. 1, an autofog nozzle 10 is illustrated, constructed in accordance with the present invention. The autofog nozzle 10 includes a main housing 12. The main housing 12 is approximately tubular in shape. An internally threaded hose coupling 14 connects a water supply hose to the downstream end of the main housing 12. The hose coupling 14 defines a plurality of external grooves 16 for ease of handling. Alternatively, the grooves 16 can be replaced by a hexagonal pattern of flats so that a tool can be used to connect or disconnect the hose. A spray ring assembly 18 is installed coaxially around the upstream end of the main housing 12. The spray ring assembly 18 defines a plurality of raised ridges 20 for easier manual rotation. A handle 22 is secured to project downwardly from a bottom side 24 of the main housing 12. The handle 22 defines a plurality of grooves 26 to aid an operator in gripping the handle. A throttle 28 is pivotally connected to two sides of the main housing above the handle 22. The throttle 28 has a grip portion 30 and two legs 32 that are perpendicular to the grip portion 30. The two legs 32 are pivotally secured on their lower ends to corresponding sides of the main housing 12.

Figure 2A:
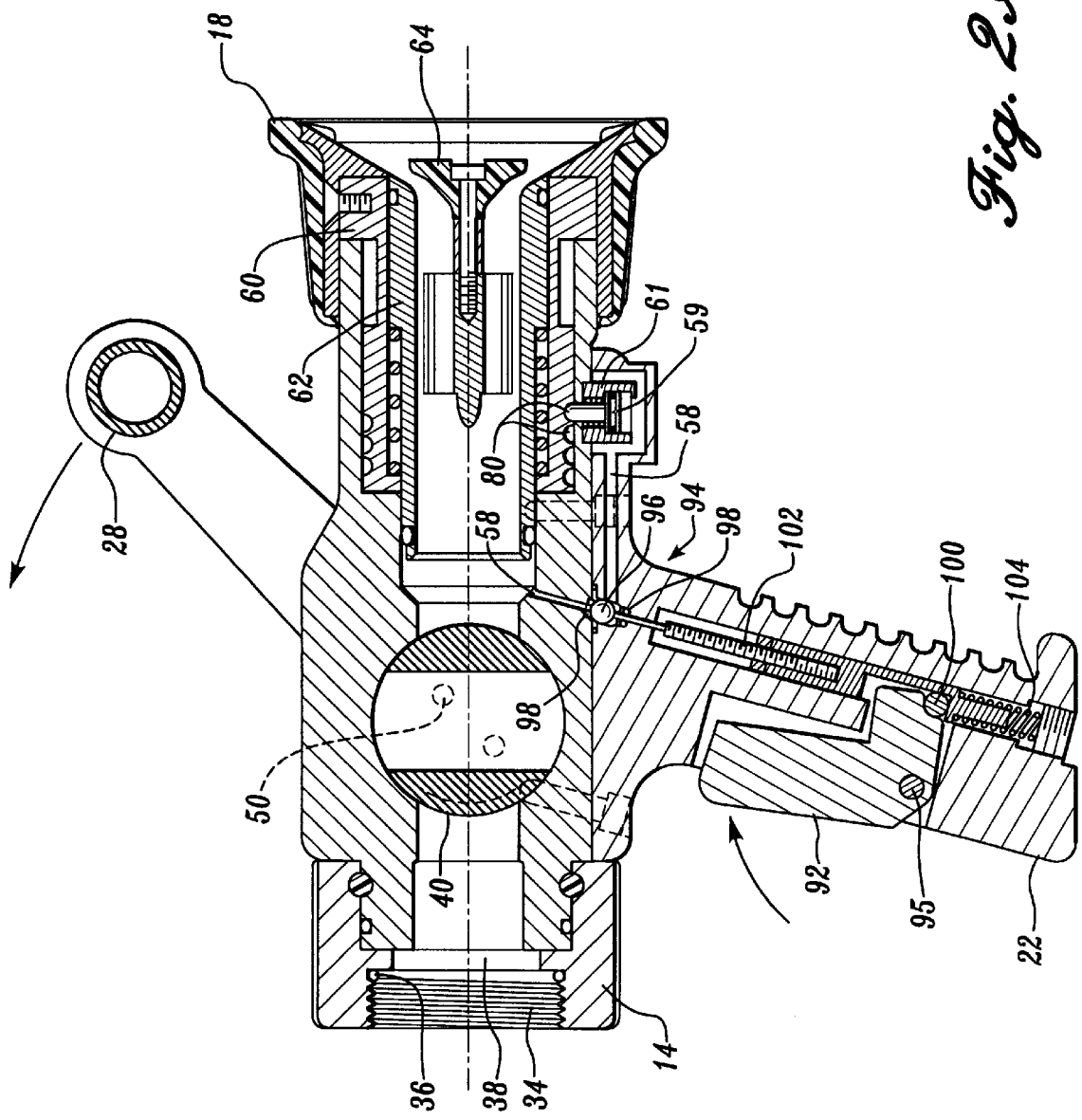
FIG. 2A is a longitudinal cross-sectional view of the autofog nozzle of FIG. 1, with a throttle in a closed position.
Figure 2B:
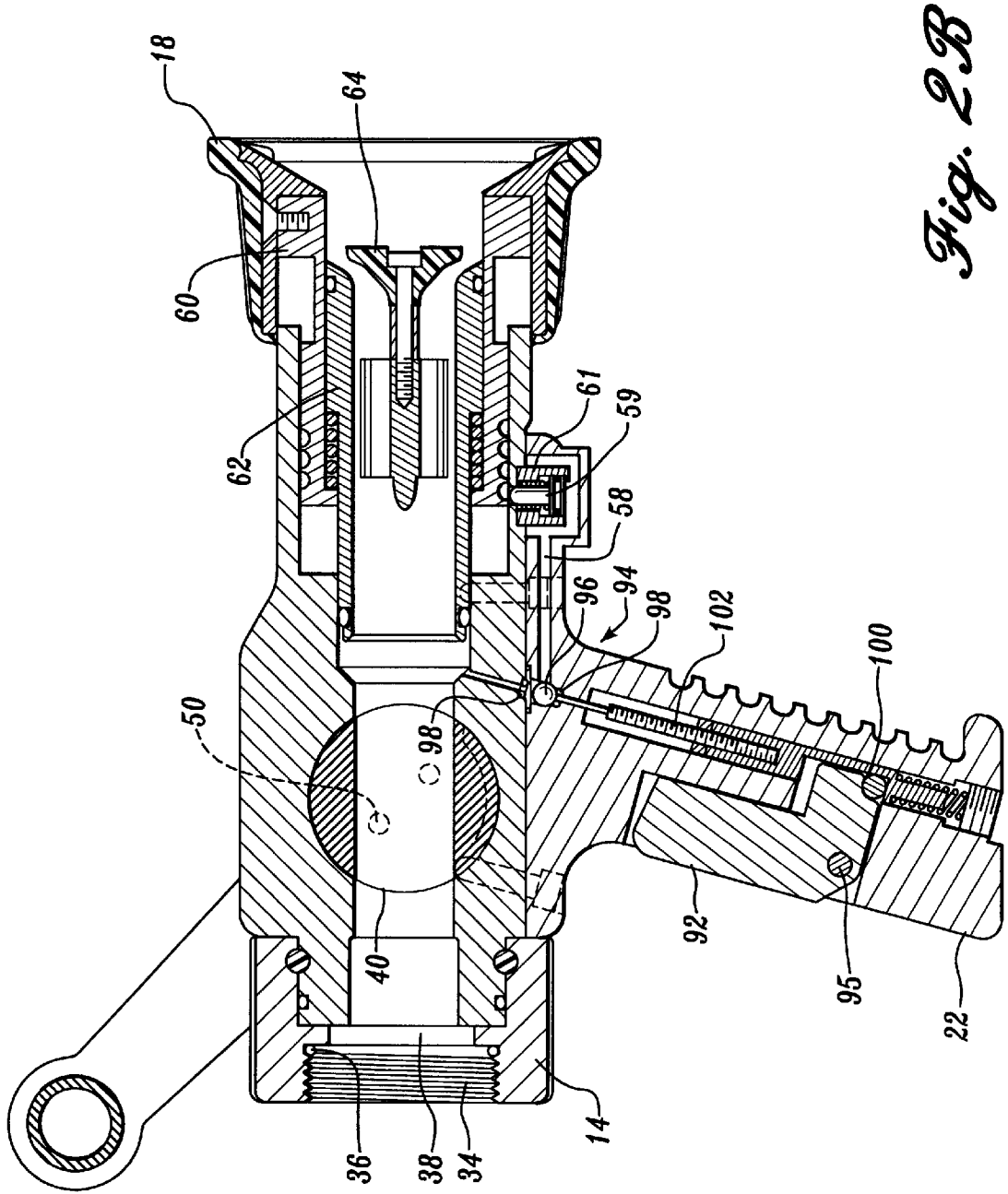
FIG. 2B is a longitudinal cross-sectional view of the autofog nozzle of FIG. 1, with the throttle in an open position.

Referring to FIGS. 2A and 2B, a water hose (not shown) is threadedly coupled to an internal thread 34 of the hose coupling 14. An elastomer seal 36 in the interior of the hose coupling 14 provides for a good seal between the hose coupling 14 and the hose. Water from the hose enters into an inner cavity 38 of the nozzle 10. The inner cavity 38 forms a natural extension of the hose.

Figure 3A:
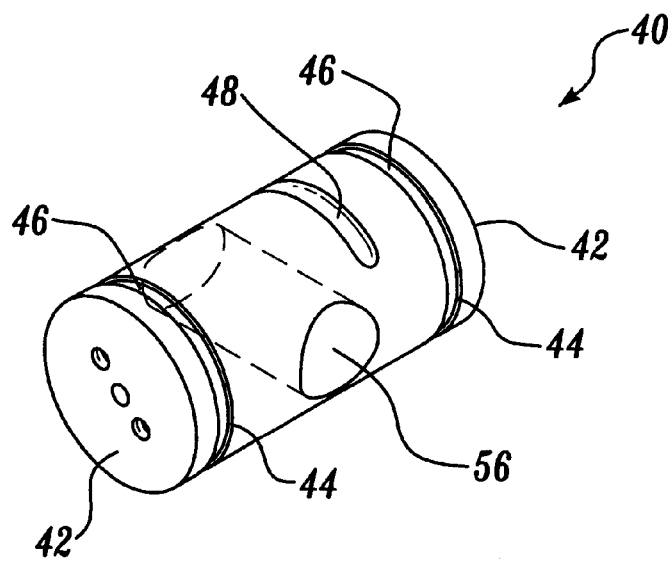
FIGS. 3A and 3B are enlarged perspective views of a plug valve included in the nozzle of FIG. 1.
Figure 3B:
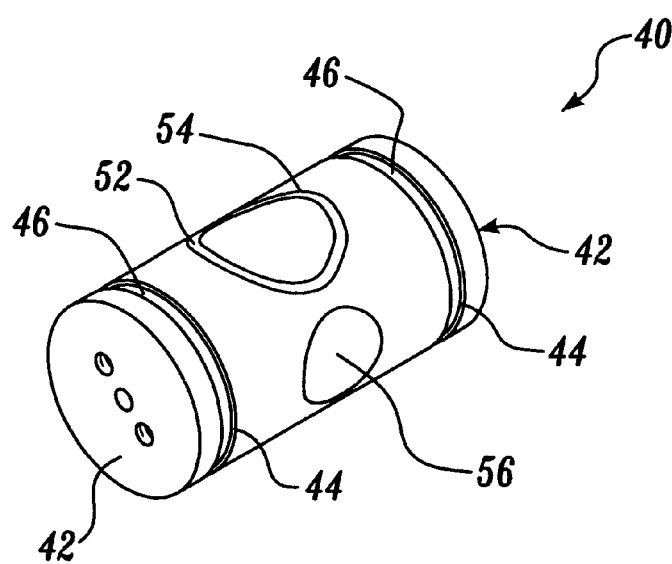

Inside the inner cavity 38, the water flows toward a cylindrical plug valve 40 that is shown in more detail in FIGS. 3A and 3B. The plug valve 40, suitably made of plastic or metal is disposed across the inner cavity 38, with its ends 42 protruding through holes in the main housing 12. The plug valve 40 has two annular grooves 44. Each annular groove 44 is adjacent to one end 42 of the plug valve 40 and is concentric with the ends 42. An elastomer seal 46 fits into each groove 44 to form a good seal with the main housing 12. The plug valve 40 also includes a groove 48 that is approximately one-fourth the length of the circumference of the plug valve 40. The groove 48 runs parallel to the annular grooves 44 and engages with a pin mounted within the housing (shown in phantom in FIGS. 2A and 2B) to limit the rotation of the plug valve 40. The plug valve 40 is attached to the two legs 32 of the throttle 28 through means of screws 50 inserted into threaded holes (not shown). Therefore, the plug valve 40 rotates when the throttle 28 is rotated by the operator.

When the throttle 28 is in a closed position as shown in FIG. 2A, the plug valve 40 blocks off the inner cavity 38, preventing water from flowing past the plug valve 40. An elastomer seal 52 recessed in a circular groove 54 on the plug valve 40 provides a good seal between the plug valve 40 and the interior of the main housing 12 to prevent water from leaking past the plug valve 40. When the throttle 28 is in an open position as shown in FIG. 2B, the plug valve 40 allows water to flow through a passage 56 running diametrically through the plug valve 40.

Figure 4A:
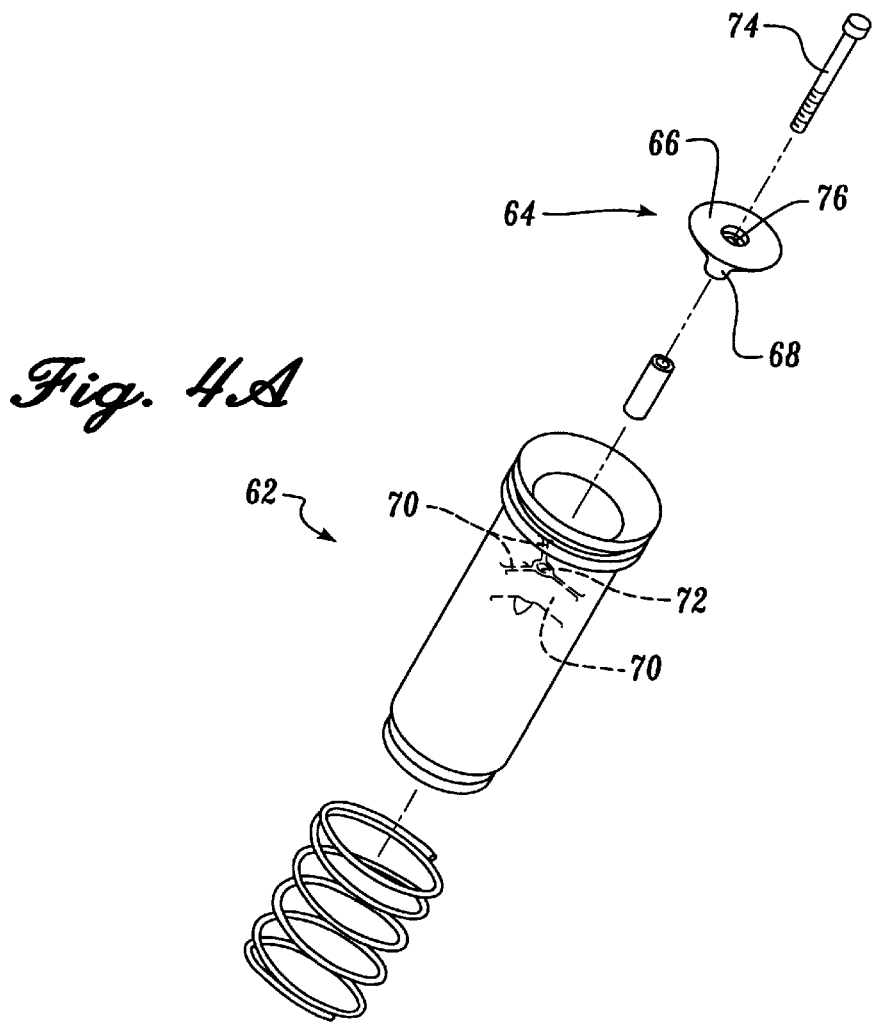
FIG. 4A is an enlarged perspective view of a carrier included in the nozzle of FIG. 1, with a barrel and a deflector shown exploded from the carrier.
Figure 4B:
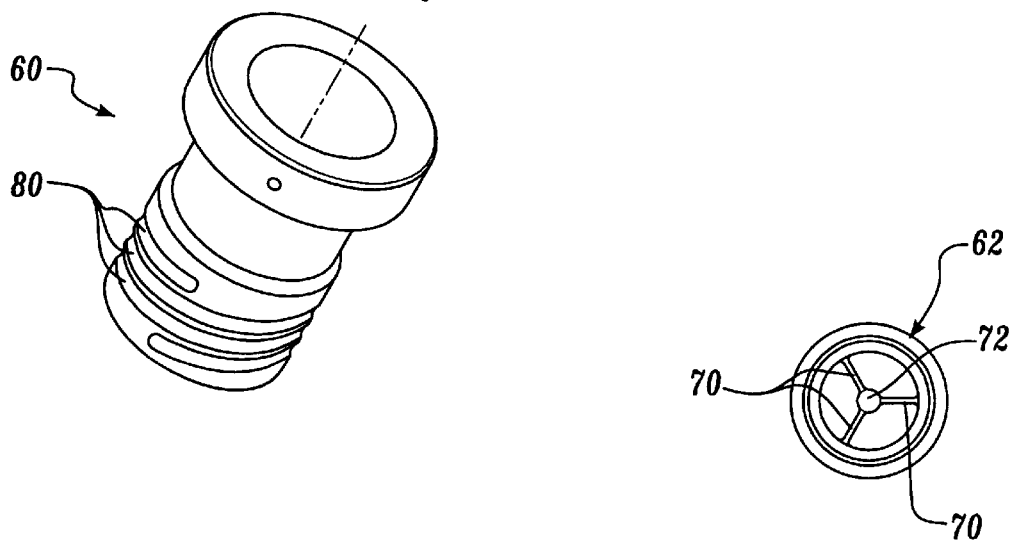
FIG. 4B is an end view of the barrel of FIG. 4A.

After the water flows past the plug valve 40, the water continues toward the upstream end of the nozzle 10. However, some of the pressure contained in the stream of water is diverted into a bypass passageway 58 that leads to a locking pin 59. The locking pin 59 is slidably mounted within a cylindrical mount 61 secured to the housing 12. The water that continues toward the upstream end of the nozzle 10 passes through a carrier 60, a barrel 62 and past a midstream-mounted, generally conical deflector 64 having a flared end 66 and a tapered mounting end 68, all shown in more detail in FIGS. 4A and 4B. The carrier 60 has at least one helical groove, but preferably has three internally formed helical grooves 80 so that the spray ring assembly 18 has to be rotated no more than one-third of a revolution before the locking pin 59 engages. The carrier 60 is suitably formed from bronze or other metal or engineering plastic, while the barrel 62 is suitably composed of aluminum or other metal or engineering plastic. Both the carrier 60 and the barrel 62 are approximately tubular in shape, with the barrel 62 disposed inside the carrier 60. The barrel 62 defines three inwardly projecting radial arms 70 in its interior for supporting the deflector 64. The arms 70 are spaced 120° apart and extend radially inward in a spoke arrangement, and are joined by a hub defining threaded aperture 72 for supporting the deflector 64. A screw 74 is inserted through a threaded aperture 76 in the flared end 66 of the deflector 64, through the mounting end 68 of the deflector 64 and into the threaded aperture 72 formed by the arms 70 to secure the deflector 64 to the barrel 62. Although the barrel 62 and the deflector 64 could alternatively be cast as one piece, it is preferable to machine them separately and assemble them for manufacturing convenience.

Figure 5A:
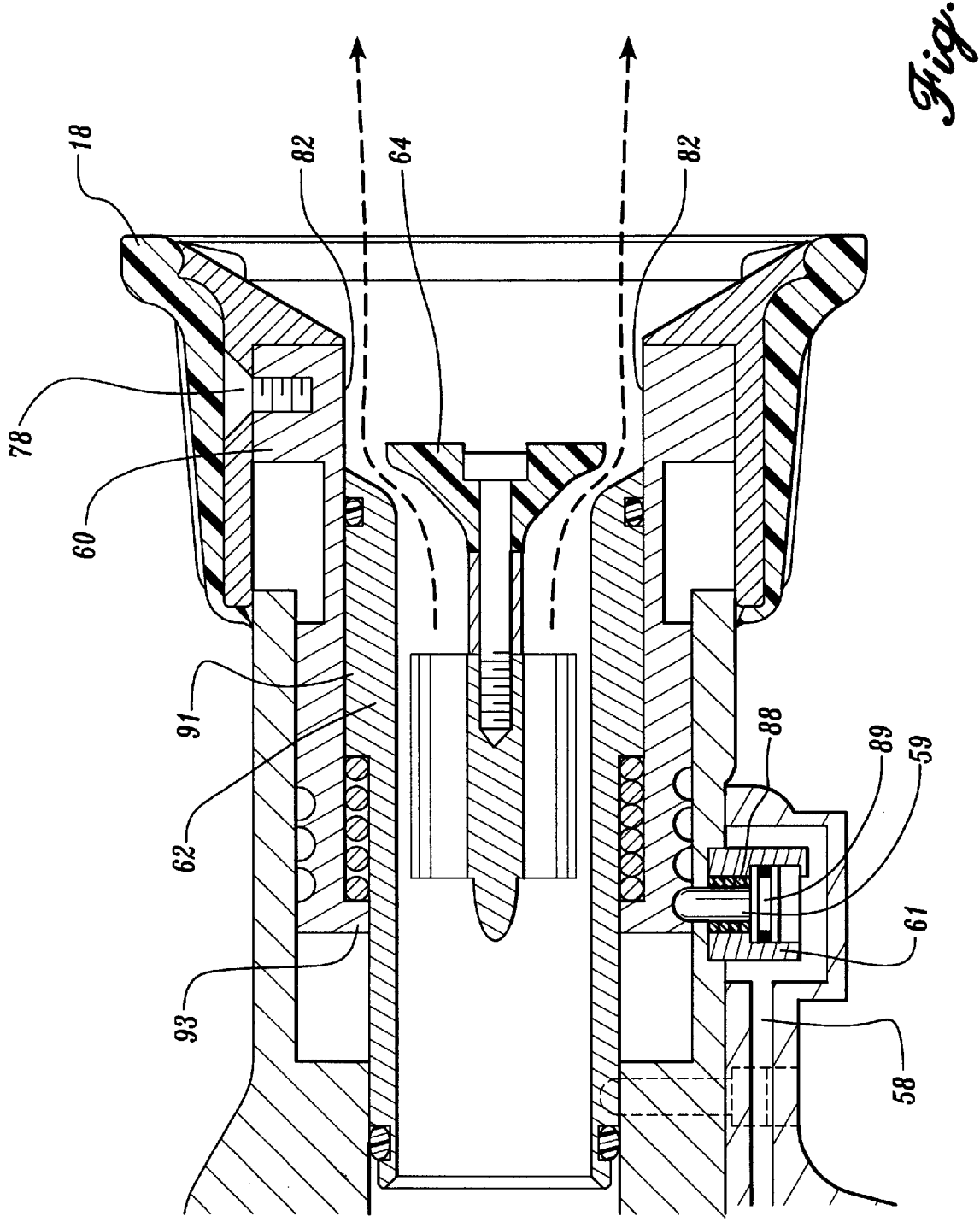
FIG. 5A is a partial, longitudinal cross-sectional view of the autofog nozzle of FIG. 1 in a jet position.
Figure 5B:
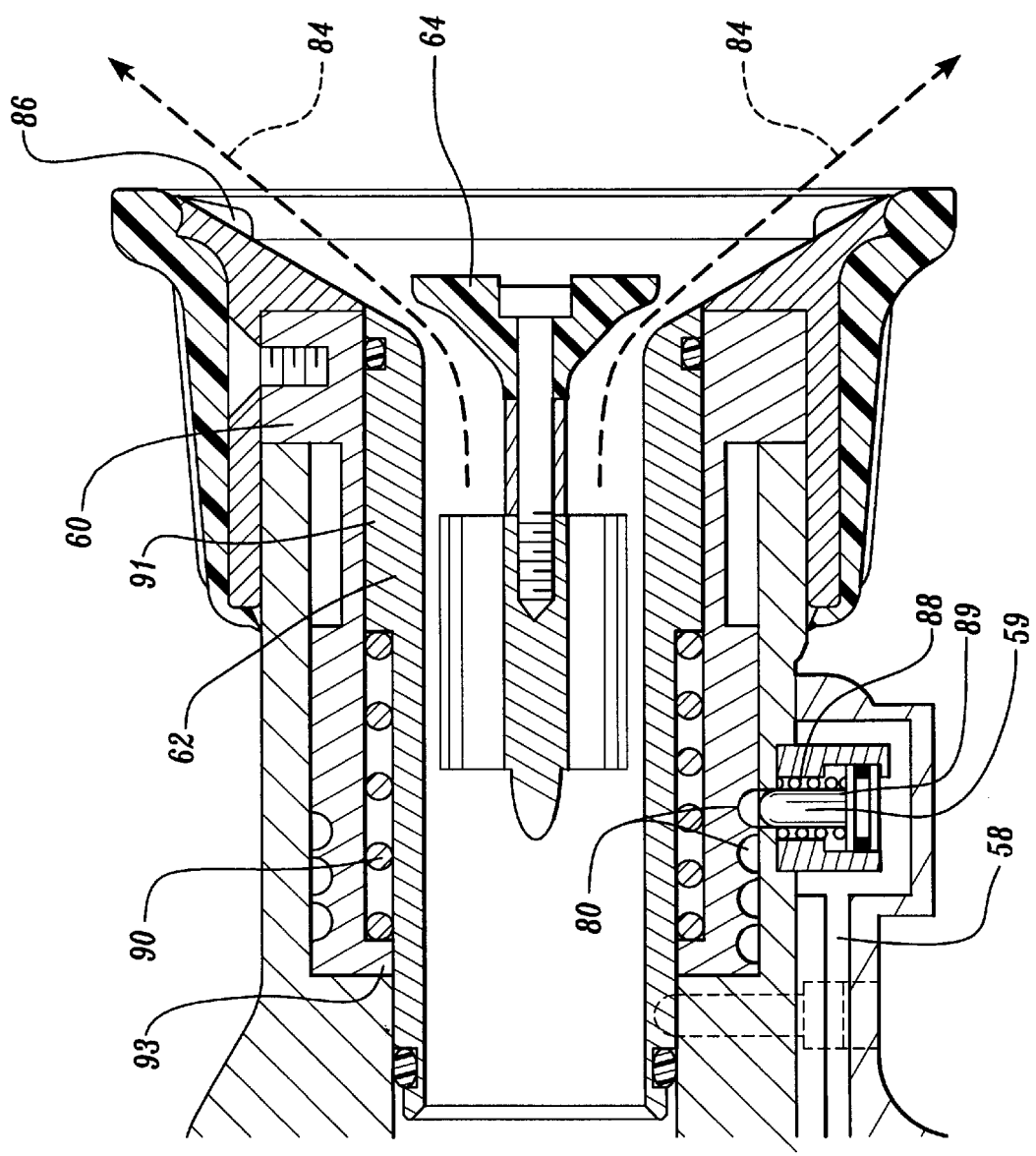
FIG. 5B is a partial, longitudinal cross-sectional view of the autofog nozzle of FIG. 1 in a fog position.

Referring to FIGS. 5A and 5B, when the operator rotates the spray ring assembly 18, the carrier 60 which is attached to the spray ring assembly 18, preferably by three screws 78 spaced 120° apart, also rotates. When the locking pin 59 is engaged in one of the three helical grooves 80 in the carrier 60 as shown in FIG. 5A, the rotation of the carrier 60 causes the spray ring assembly 18 and the carrier 60 to translate forward as shown in FIG. 5A or to retract as shown in FIG. 5B, depending on the direction of the rotation. In either case, the barrel 62 and the deflector 64 remain translationally stable. (The engagement of the locking pin 59 will be discussed in more detail later.)

When the carrier 60 and the spray ring assembly 18 translate forward, as shown in FIG. 5A, the nozzle 10 is in the jet position. The stream of water is focused by straight sides 82 of the interior surface of the carrier 60 immediately before exiting the nozzle 10. Therefore, a concentrated, converged jet stream of water is emitted from the nozzle 10, as indicated by the directional arrows.

When the carrier 60 and the spray ring assembly 18 are retracted, as shown in FIG. 5B, the nozzle 10 is in the fog position The deflector 64 and the slanted front edge 84 of the barrel 62 form a path that diverges outwardly. Therefore, the stream of water is directed outwardly immediately before exiting the nozzle 10 to form a less concentrated water spray or fog, as indicated by the directional arrows. Fins 86, or raised notches, placed in a circular arrangement around the front end of the spray ring assembly 18 help disperse the water.

Still referring to FIGS. 5A and 5B, when water pressure is supplied to the nozzle 10 for use, the diverted water pressure in the bypass passageway 58 biases the locking pin 59 upward to engage one of the three helical grooves 80 in the carrier 60 as shown in FIG. 5A. The force of the water pressure is sufficient to compress a locking pin bias spring 88 recessed on the pin 59 and captured between a head 89 of the pin 59 and the housing 12. Rotation of the spray ring assembly 18 by the operator thus results in the rotation of the carrier 60. When the locking pin 59 is engaged, rotation of the carrier 60 causes the carrier, and thus also the spray ring 18, to either translate forward or to retract, depending on the direction of the rotation.

If the water pressure drops below a predetermined level, the locking pin bias spring 88 around the locking pin 59 causes the locking pin 59 to retract and disengage from the groove 80 in the carrier 60 as shown in FIG. 5B. When the locking pin 59 retracts and thereby releases the carrier 60, a compression coil carrier spring 90 mounted around the barrel 62 extends, forcing the carrier 60 and the spray ring assembly 18 to retract to the fog position. The carrier spring 90 is captured between a raised annular portion 91 of the barrel 62 and an annular flange 93 of the carrier 60. Furthermore, when the locking pin 59 is in the retracted position, rotation of the spray ring assembly 18 merely causes rotation of the carrier 60, but will not cause translation of the carrier 60 and the spray ring assembly 18. Therefore, when there is a loss of water pressure, the spray ring assembly 18 automatically assumes the fog position and the operator cannot manually return the spray ring assembly 18 to the jet position until water pressure is restored.

Loss of water pressure may occur by intentional or unintentional shutting-off of water. Automatic return to the fog position prevents the unintentional occurrence of a hazardous jet stream when water pressure is restored.

Referring back to FIGS. 2A and 2B, in the preferred embodiment, the nozzle 10 also includes a safety lever 92 that controls a spring-loaded control valve 94 interposed in the bypass passageway 58 leading to the locking pin 59. The safety lever 92 is located inside the handle 22, slightly protruding from the handle 22. The control valve 94 consists of a ball 96 that seats against either of two elastomer seals 98. When the operator depresses the safety lever 92 as shown in FIG. 2B, the safety lever pivots on a pin 95 and pushes down on a ball bearing 100 which in turn pushes down on a longitudinally adjustable piston assembly 102 on which the ball 96 rests. When the ball 96 drops below the bypass passageway 58 as shown in FIG. 2B, the ball 96 seats against the lower elastomer seal 98, and the water pressure can be diverted through the remainder of the bypass passageway 58 to the locking pin 59 to engage the locking pin 59.

If the operator releases the safety lever 22 as shown in FIG. 2A, a control valve bias spring 104 mounted on the lower end of the piston assembly 102 extends to push the piston upward, thereby pushing the ball 96 upward to seat against the upper elastomer seal 98 to block the bypass passageway 58. When the bypass passageway 58 is blocked, a loss of water pressure to the locking pin 59 occurs as water drains from the bypass passageway 58 through the handle and the nozzle 10 automatically assumes the fog position.

While the preferred embodiment of the invention has been illustrated and described, it will be appreciated that various changes can be made therein without departing from the spirit and scope of the invention. For example, the nozzle can be a hand held version as described above, or can be a stationary mounted monitor version. In the stationary mounted monitor version, there is no need for a safety lever and control valve because the mere presence of a pressured flow will cause the pin to engage when the spray ring is rotated. If the pressure falls below a certain point, then the locking pin is automatically disengaged by the bias spring. Furthermore, the throttle is optional in the stationary mounted monitor version.

The embodiments of the invention in which an exclusive property or privilege is claimed are defined as follows:

1. A nozzle for emitting a fluid, the nozzle comprising:
   a main housing couplable to a water supply and defining an internal fluid flow passage and including an engagement member mounted within the main housing;
   a stationary fluid flow deflector mounted centrally within the main housing and fluid flow passage; and
   a tubular body, having an engaging surface, at least partially surrounding the fluid flow deflector and alignable for engagement with the engagement member of the main housing, wherein the engagement member is engaged when fluid is supplied to the nozzle and the engagement member is disengaged when the fluid pressure in the nozzle falls below a predetermined level, and wherein the tubular body translates longitudinally relative to the stationary fluid flow deflector to a jet position when the tubular body is rotated in a first direction while the engagement member is engaged and translates longitudinally to a fog position when the tubular body is rotated in a second direction while the engagement member is engaged.

2. The nozzle of claim 1, wherein the engagement member is a locking pin that is biased by fluid pressure to engage the engaging surface of the tubular body.

3. The nozzle of claim 2, wherein a locking pin bias spring disposed in a bypass passageway causes the locking pin to disengage when fluid pressure in the nozzle falls below a predetermined level.

4. The nozzle of claim 1, wherein a biasing member causes the tubular body to translate to the fog position when the engagement member is disengaged.

5. The nozzle of claim 4, wherein the biasing member comprises a coil spring.

6. The nozzle of claim 1, further comprising a control valve for selectively blocking fluid pressure to the engagement member, thereby disengaging the engagement member from the tubular body.

7. The nozzle of claim 1, further comprising a bypass channel defined by the housing that places the internal fluid flow passage in communication with the engagement member to control movement of the engagement member wherein a control valve is disposed within the bypass channel.

8. The nozzle of claim 7, wherein the control valve is disposed in a handle assembly and selectively rests against an upper seat or a lower seat.

9. The nozzle of claim 1, wherein the engaging surface is a helical groove.

10. The nozzle of claim 9, wherein the helical groove comprises a plurality of helical grooves.

11. The nozzle of claim 1, further comprising a stationary inner tubular body supporting the fluid flow deflector.

12. A nozzle for emitting a fluid, the nozzle comprising:
    a main housing couplable to a water supply and defining an internal fluid flow passage and including an engagement member mounted within the main housing;
    a stationary fluid flow deflector mounted within the main housing and the fluid flow passage;
    a translating tubular body, having an engaging surface, alignable for engagement with the engagement member of the main housing; and
    a fluid pressure operated valve to move the engagement member when fluid pressure is supplied.

13. The nozzle of claim 12, wherein the fluid pressure operated valve is a locking pin for engaging the engaging surface when fluid pressure is supplied and a compression coil biased to disengage the locking pin from the engaging surface when fluid pressure falls below a predetermined level.

14. A nozzle for emitting a fluid, the nozzle comprising:
    a main housing couplable to a water supply and defining an internal fluid flow passage and including an engagement member mounted within the main housing;
    a stationary fluid flow deflector mounted within the main housing and fluid flow passage; and
    a tubular body, having an engaging surface, alignable for engagement with the engagement member of the main housing, wherein the engagement member is engaged when fluid is supplied to the nozzle and the engagement member is disengaged when the fluid pressure in the nozzle falls below a predetermined level, and wherein the tubular body selectively translates longitudinally relative to the stationary fluid flow deflector to either a jet position or a fog position while the engagement member is engaged.

15. A nozzle for emitting a fluid, the nozzle comprising:
    a main housing couplable to a water supply including an engagement member mounted within the main housing;
    a stationary fluid flow deflector mounted centrally within the main housing; and
    a tubular body movably mounted on the housing coaxially with the fluid flow deflector and cooperating with the fluid flow deflector and selectively movable when the engagement member is engaged upon supply of fluid to the nozzle to form a converging flow cavity for emitting a concentrated jet stream of fluid or a diverging flow cavity for emitting a dispersed spray of fluid.

* * * * *

UNITED STATES PATENT AND TRADEMARK OFFICE
CERTIFICATE OF CORRECTION

PATENT NO. : 6,007,001
DATED : December 28, 1999
INVENTOR(S) : T.J. Hilton

It is certified that error appears in the above-identified patent and that said Letters Patent is hereby corrected as shown below:

COLUMN    LINE

[73]              Assignee              "Amhi Corporation" should read
Pg. 1, col. 1                           --Amhi Corporation d.b.a. A & H Enterprises--

Pg. 1, col. 2     Attorney,             "Christrensen" should read --Christensen--
                  Agent, or Firm Signed and Sealed this Twenty-fourth Day of April, 2001

Attest:

NICHOLAS P. GODICI

Attesting Officer    Acting Director of the United States Patent and Trademark Office